United States Patent
Grauert et al.

(10) Patent No.: US 6,355,652 B1
(45) Date of Patent: Mar. 12, 2002

(54) SUBSTITUTED 1,2,3,4,5,6-HEXAHYDRO-2,6-METHANO-3-BENZAZOCINES AND THEIR USE AS PHARMACEUTICAL COMPOSITIONS

(75) Inventors: Matthias Grauert, Ingelheim; Adrian Carter, Bingen; Thomas Weiser, Nieder-Olm; Helmut Ensinger; Wolfram Gaida, both of Ingelheim; Joachim Mierau, Mainz, all of (DE)

(73) Assignee: Boehringer Ingelheim Pharma KG, Ingelheim (DE)

( * ) Notice: Subject to any disclaimer, the term of this patent is extended or adjusted under 35 U.S.C. 154(b) by 0 days.

(21) Appl. No.: 09/699,748

(22) Filed: Oct. 30, 2000

Related U.S. Application Data

(60) Provisional application No. 60/169,864, filed on Dec. 9, 1999.

(30) Foreign Application Priority Data

Nov. 27, 1999 (DE) .......................... 199 57 156

(51) Int. Cl.[7] ..................... A61K 31/439; C07D 221/22

(52) U.S. Cl. ......................................... 514/295; 546/97

(58) Field of Search ............................. 514/295; 546/97

(56) References Cited

U.S. PATENT DOCUMENTS 5,607,941 A * 3/1997 Merz et al. ................. 514/289
5,731,318 A * 3/1998 Carter et al. ................ 514/289

FOREIGN PATENT DOCUMENTS

| CA | 2072814 | 1/1993 |
|---|---|---|
| EP | 0521422 | 1/1993 |
| WO | WO 9914199 | 9/1999 |
| WO | WO 0050421 | 8/2000 |

* cited by examiner

*Primary Examiner*—Charanjit S. Aulakh
(74) *Attorney, Agent, or Firm*—Robert P. Raymond; Alan R. Stempel; Mary-Ellen M. Devlin

(57) ABSTRACT

Substituted 1,2,3,4,5,6-hexahydro-2,6-methano-3-benzazocines of general formula 1:

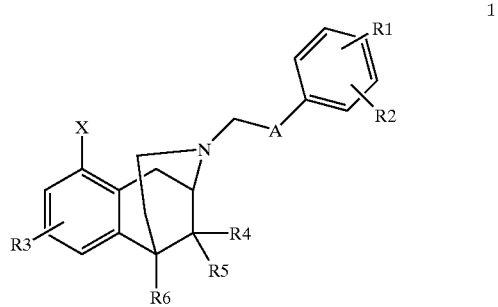

wherein:

$R^1$ and $R^2$, which may be identical or different, are each hydrogen, $C_1$–$C_6$-alkyl, $C_1$–$C_6$-alkyloxy, OH, F, Cl, or Br;

$R^3$ is hydrogen, F, Cl, Br, methyl, ethyl, OH, or methoxy;

$R^4$, $R^5$, and $R^6$, which may be identical or different, are each hydrogen, methyl, or ethyl;

X is $NH_2$, NH-($C_1$–$C_6$-alkyl), N($C_1$–$C_6$-alkyl)$_2$, the two $C_1$–$C_6$-alkyl groups of which may be identical or different, NH—COH, NH—CO($C_1$–$C_6$-alkyl), or F;

A is —(CH$_2$)$_3$—, —CH$_2$—CH$_2$—O—, —CH$_2$—O—CH$_2$—, —(CH$_2$)$_4$—, —CH($C_1$–$C_6$-alkyl)-O—CH$_2$—, —(CH$_2$)$_2$—O—CH$_2$13 , —(CH$_2$)$_3$—O—, —(CH$_2$)$_5$—, —CH$_2$—O—(CH$_2$)$_3$—, —(CH$_2$)$_2$—O—(CH$_2$)$_2$—, —(CH$_2$)$_3$—O—CH$_2$—, —(CH$_2$)$_4$—O—, —CH$_2$—O—CH$_2$—CH$_2$—O—,

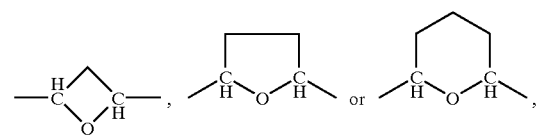

the racemates thereof, the enantiomers thereof, the diastereomers thereof, and mixtures thereof, and the pharmacologically acceptable acid addition salts thereof, processes for preparing them, and their use as pharmaceutical compositions.

14 Claims, No Drawings

SUBSTITUTED 1,2,3,4,5,6-HEXAHYDRO-2,6-METHANO-3-BENZAZOCINES AND THEIR USE AS PHARMACEUTICAL COMPOSITIONS

RELATED APPLICATION

This application claims the benefit of U.S. Provisional Application Ser. No. 60/169,864, filed Dec. 9, 1999.

BACKGROUND OF THE INVENTION

The present invention relates to substituted 1,2,3,4,5,6-hexahydro-2,6-methano-3-benzazocines of general formula 1

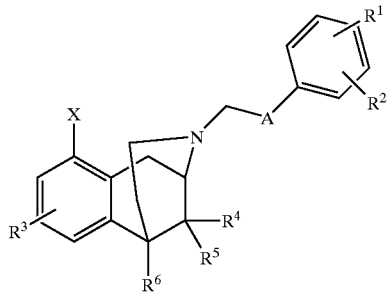

wherein $R_1$ and $R^2$ which may be identical or different denote hydrogen, $C_1$–$C_6$-alkyl, $C_1$–$C_6$-alkyloxy, OH, F, Cl, or Br;

$R^3$ may denote hydrogen, F, Cl, Br, methyl, ethyl, OH, or methoxy;

$R^4$, $R^5$, and $R^6$, which may be identical or different, may denote hydrogen, methyl, or ethyl;

X may denote $NH_2$, NH-($C_1$–$C_6$-alkyl), N($C_1$–$C_6$-alkyl)$_2$, the two $C_1$–$C_6$-alkyl groups of which may be identical or different, NH—COH, NH—CO($C_1$–$C_6$-alkyl), or F;

A may denote —(CH$_2$)$_3$—, —CH$_2$—CH$_2$—O—, —CH$_2$—O—CH$_2$—, —(CH$_2$)$_4$—, —CH($C_1$–$C_6$-alkyl)-O—CH$_2$—, —(CH$_2$)$_2$—O—CH$_2$—, —(CH$_2$)$_3$—O—, (CH$_2$)$_5$—, —CH$_2$—O—(CH$_2$)$_3$—,

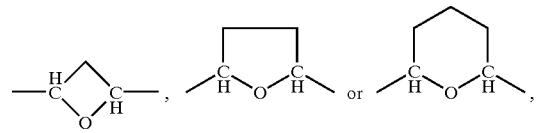

optionally in the form of their racemates, their enantiomers, their diastereomers and mixtures thereof, and optionally the pharmacologically acceptable acid addition salts thereof.

Preferred compounds are those of general formula 1, wherein:

$R_1$ and $R^2$ which may be identical or different, denote hydrogen, methyl, ethyl, methyloxy, ethyloxy, OH, F, Cl, or Br;

$R^3$ may denote hydrogen, F, methyl, ethyl, OH, or methoxy;

$R^4$, $R^5$, and $R^6$, which may be identical or different, may denote hydrogen or methyl;

X may denote $NH_2$, NH-(methyl), N(methyl)$_2$, NH-(ethyl), N(ethyl)$_2$, NH—COH, NH—COMe, or F;

A may denote —CH$_2$—CH$_2$—O—, —CH$_2$—O—CH$_2$—, —CH(methyl)-O—CH$_2$—, CH(ethyl)-O—CH$_2$—, —CH(isopropyl)-O—CH$_2$—, —(CH$_2$)$_2$—O—CH$_2$—, —(CH$_2$)$_3$—O—, —CH$_2$—O—(CH$_2$)$_3$—, —(CH$_2$)$_2$—O—(CH$_2$)$_2$—, —(CH$_2$)$_3$—O—CH$_2$—, —(CH$_2$)$_4$—O—, —CH$_2$—O—CH$_2$—CH$_2$—

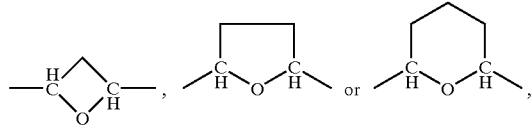

optionally in the form of their racemates, their enantiomers, their diastereomers and mixtures thereof, and optionally the pharmacologically acceptable acid addition salts thereof.

Particularly preferred are compounds of general formula 1, wherein:

$R_1$ and $R^2$ which may be identical or different, may denote hydrogen or F;

$R^3$ may denote hydrogen or methyl;

$R^4$, $R^5$, and $R^6$, which may be identical or different, may denote hydrogen or methyl;

X may denote $NH_2$, NH-(methyl), N(methyl)$_2$, NH—COH, or NH—COMe;

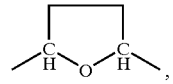

A may denote —CH(methyl)-O—CH$_2$—, —CH$_2$—O—CH$_2$—, or optionally in the form of their racemates, their enantiomers, their diastereomers and mixtures thereof, and optionally the pharmacologically acceptable acid addition salts thereof.

Of comparable importance according to the invention are compounds of general formula 1 wherein:

$R^1$ and $R^2$ which may be identical or different may denote hydrogen or F;

$R^3$ may denote hydrogen;

$R^4$, $R^5$, and $R^6$, which may be identical or different, may denote hydrogen or methyl;

X may denote F;

A may denote —CH(methyl)-O—CH$_2$—, optionally in the form of their racemates, their enantiomers, their diastereomers and mixtures thereof, and optionally the pharmacologically acceptable acid addition salts thereof.

Of particular interest are compounds of general formula 1 selected from the group comprising:

(2R,6S,2S')-10-amino-3-[2(2,6-difluorophenylmethoxy) propyl]-1,2,3,4,5,6-hexahydro-6,11,11-trimethyl-2,6-methano-3-benzazocine dihydrochloride;

(2R,6S,2S')-10-amino-3-[2-(benzyloxy)propyl]-1,2,3,4,5,6-hexahydro-6,11,11trimethyl-2,6-methano-3-benzazocine dihydrochloride;

(2R,6S,11R,2"S)-10-amino-3-[2(2,6-difluorophenylmethoxy)propyl]-1,2,3,4,5,6-hexahydro-6,11-dimethyl-2,6-methano-3-benzazocine dihydrochloride;

(2R,6S,11S,2"S)-10-amino-3-[2(2,6-difluorophenylmethoxy)propyl]-1,2,3,4,5,6-hexahydro-6,11-dimethyl-2,6-methano-3-benzazocine dihydrochloride;

(2R,6S)-10-amino-3-[2(2,6-difluorophenylmethoxy)ethyl]-1,2,3,4,5,6-hexahydro-6,11,11-trimethyl-2,6-methano-3-benzazocine dihydrochloride;

(2R,6S,2"S,5"S)-10-amino-3-[5"-phenyltetrahydrofuran-2"-yl)methyl]-1,2,3,4,5,6-hexahydro-6,11,11-trimethyl-2,6-methano-3-benzazocine dihydrochloride;

(2R,6S,2"S)-10-acetamino-3-[2(benzyloxy)propyl]-1,2,3,4,5,6-hexahydro-6,11,11-trimethyl-2,6-methano-3-benzazocine hydrochloride;

(2R,6S,2"S)-10-acetamino-3-[2(2,6-difluorophenylmethoxy)propyl]-1,2,3,4,5,6-hexahydro-6,11,11-trimethyl-2,6-methano-3-benzazocine hydrochloride;

(2R,6S,2"S)-10-formylamino-3-[2(2,6-difluorophenylmethoxy)propyl]-1,2,3,4,5,6-hexahydro-6,11,11-trimethyl-2,6-methano-3-benzazocine hydrochloride;

(2R,6S,2"S)-10-methylamino-3-[2(2,6-difluorophenylmethoxy)propyl]-1,2,3,4,5,6-hexahydro-6,11,11-trimethyl-2,6-methano-3-benzazocine dihydrochloride;

(2R,6S,2"S)-10-dimethylamino-3-[2(2,6-difluorophenylmethoxy)propyl]-1,2,3,4,5,6-hexahydro-6,11,11-trimethyl-2,6-methano-3-benzazocine dihydrochloride; and (2R,6S,2"S)-10-ethylamino-3-[2(2,6-difluorophenylmethoxy)propyl]-1,2,3,4,5,6-hexahydro-6,11,11-trimethyl-2,6-methano-3-benzazocine dihydrochloride.

$C_1$–$C_6$-alkyl denotes a branched or unbranched hydrocarbon group having 1 to 6 carbon atoms which may optionally also contain ring systems. The alkyl substituents may be identical or different and may optionally be substituted with one or more halogen atoms, preferably fluorine. Examples include methyl, ethyl, propyl, isopropyl, butyl, isobutyl, pentyl, isopentyl, neopentyl, hexyl, cyclopropylmethyl, cyclobutyl, cyclopentyl, and cyclohexyl. In some cases, common abbreviations are also used for the abovementioned alkyl groups, such as, for example, Me for methyl, Et for ethyl, prop for propyl, etc.

According to the invention, the double-bonded groups representing group A may be linked to the adjacent groups in both possible orientations.

If desired, the compounds of general formula 1 may be converted into the salts thereof, particularly, for pharmaceutical use, into the pharmacologically acceptable acid addition salts thereof with an inorganic or organic acid. Suitable acids for this purpose include, for example, succinic acid, hydrobromic acid, acetic acid, fumaric acid, maleic acid, methanesulphonic acid, lactic acid, phosphoric acid, hydrochloric acid, sulfuric acid, tartaric acid, or citric acid. Mixtures of the abovementioned acids may also be used.

The compounds according to the invention are blockers of the voltage-dependent sodium channel. They are compounds which competitively or non-competitively displace batrachotoxin (BTX) with a high affinity ($K_i$<1000 nM) from the binding site on the sodium channel. Such substances exhibit "use-dependency" in blocking the sodium channels, i.e., in order for the substances to bind to the sodium channel the sodium channels first have to be activated. The maximum blockade of the sodium channels is only achieved after repeated stimulation of the sodium channels. Consequently, the substances preferentially bind to sodium channels which are activated repeatedly.

As a result, the substances are capable of acting preferentially in those parts of the body which are pathologically overstimulated. This includes diseases such as arrhythmias, spasms, cardiac and cerebral ischaemia, pain and neurodegenerative diseases of various origins. The following may be mentioned, for example: epilepsy, hypoglycaemia, hypoxia, anoxia, brain trauma, brain oedema, cerebral stroke, perinatal asphyxia, degeneration of the cerebellum, amyotrophic lateral sclerosis, Huntington's disease, Alzheimer's disease, Parkinson's disease, cyclophrenia, hypotonia, cardiac infarct, heart rhythm disorders, angina pectoris, chronic pain, neuropathic pain, and local anesthesia.

Another aspect of the invention therefore relates to the use of compounds of general formula 1 as pharmaceutical compositions, particularly as pharmaceutical compositions in which the blockade of the voltage-dependent sodium channel may have a therapeutic value.

The compounds of general formula 1 according to the invention are preferably used to prepare a pharmaceutical composition for the prevention or treatment of arrhythmias, spasms, cardiac and cerebral ischaemias, pain, and neurodegenerative disorders.

The compounds of general formula 1 according to the invention are most preferably used as hereinbefore to prepare pharmaceutical compositions for the prevention or treatment of epilepsy, hypoglycaemia, hypoxia, anoxia, brain trauma, brain oedema, cerebral stroke, perinatal asphyxia, degeneration of the cerebellum, amyotrophic lateral sclerosis, Huntington's disease, Alzheimer's disease, Parkinson's disease, cyclophrenia, hypotonia, cardiac infarct, heart rhythm disorders, angina pectoris, chronic pain, neuropathic pain, and local anesthesia.

The test system used to detect the blocking effect on the sodium channel is the BTX binding to the sodium channel [S. W. Postma & W. A. Catterall, *Mol. Pharmacol.*, 25, 219–227 (1984)] and patch-clamp experiments which can be used to show that the compounds according to the invention block the electrically stimulated sodium channel in a "use-dependent" manner [W. A. Catterall, *Trends Pharmacol. Sci.*, 8, 57–65 (1987)]. The effect of the substances on various subtypes of sodium channel can be investigated by suitable selection of the cell system (e.g., neuronal, cardiac, DRG cells).

The sodium channel blocking property of the compounds according to the invention can be demonstrated by the blockade of the veratridine-induced glutamate release [S. Villanueva, P. Frenz, Y. Dragnic, and F. Orrego, *Brain Res.*, 461, 377–380 (1988)]. Veratridine is a toxin which permanently opens the sodium channel. As a result, there is an increased influx of sodium ions into the cell. By means of the cascade described above, this sodium influx in the neuronal tissue leads to an increased glutamate release. The compounds according to the invention will antagonize this glutamate release.

The anticonvulsant properties of the substances according to the invention have been demonstrated by their protective effect against convulsions induced by a maximum electric shock in mice [M. A. Rogawski & R. J. Porter, *Pharmacol. Rev.*, 42, 223–286 (1990)].

Neuroprotective properties have been demonstrated by the protective effect in a rat-MCAO model [U. Pschorn & A. J. Carter, *J. Stroke Cerebrovascular Diseases*, 6, 93–99 (1996)], a malonate-induced lesion model [M. F. Beal, *Annals of Neurology*, 38, 357–366 (1995) and J. B. Schulz, R. T. Matthews, D. R. Henshaw, and M. F. Beal, *Neuroscience*, 71, 1043–1048 (1996)] and an MPTP-induced degeneration model [J. P. Steiner, et al. *Proc. Natl. Acad. Sci.*, 94, 2019–2024 (1997)].

The analgesic effect was shown in a formalin-induced pain model [D. Dubuisson and S. G. Dennis, *Pain*, 4, 161–174 (1977)] and in a ligature model [G. J. Bennett & Y.-K. Xie, *Pain*, 33, 87–107 (1988)].

It has also been shown that sodium channel blockers can be used to treat cyclophrenia (manic depressive disease) [J. R. Calabrese, C. Bowden, and M. J. Woyshville, in: *Psychopharmacology: The Fourth Generation of Progress* (Eds. D. E. Bloom and D. J. Kupfer) 1099–1111, New York: Raven Press Ltd.].

The compounds according to the invention 1 may be prepared analogously to methods of synthesis known per se. One possible method of synthesis is shown in Diagram 1. The 1,2,3,4,5,6-hexahydro-2,6-methano-3-benzazocin-10-ols (2) designated as starting compounds in Diagram 1 may be obtained by methods of synthesis known from the art. In connection with this, reference is made at this point to European Patent Application EP 521422 and to International Patent Applications WO 97/06146 and WO 99/14199.

drofuran. Methylene chloride should be mentioned as being particularly preferred. The reactions to form the triflates 3 are preferably carried out at temperatures below ambient temperature, more preferably at $-50°$ C. to $0°$ C., most preferably at between $-30°$ C. and $-5°$ C. After 0.5 to 4 hours, stirring is continued at ambient temperature until the reaction is complete (about 1 to 12 hours). After working up, the crude products 3 thus obtained are reacted, without further purification, in an aromatic organic solvent, preferably selected from among toluene, benzene, or xylene, most preferably toluene, with palladium as catalyst, preferably in the presence of a phosphine ligand, with a nitrogen source, preferably with ketimines, most preferably with benzophenonimine. Suitable palladium catalysts according to the invention include tris(dibenzylideneacetone)dipalladium(0), palladium(II) acetate, or tetrakis(triphenylphosphine) palladium(0), for example. Suitable phosphine ligands Diagram 1:

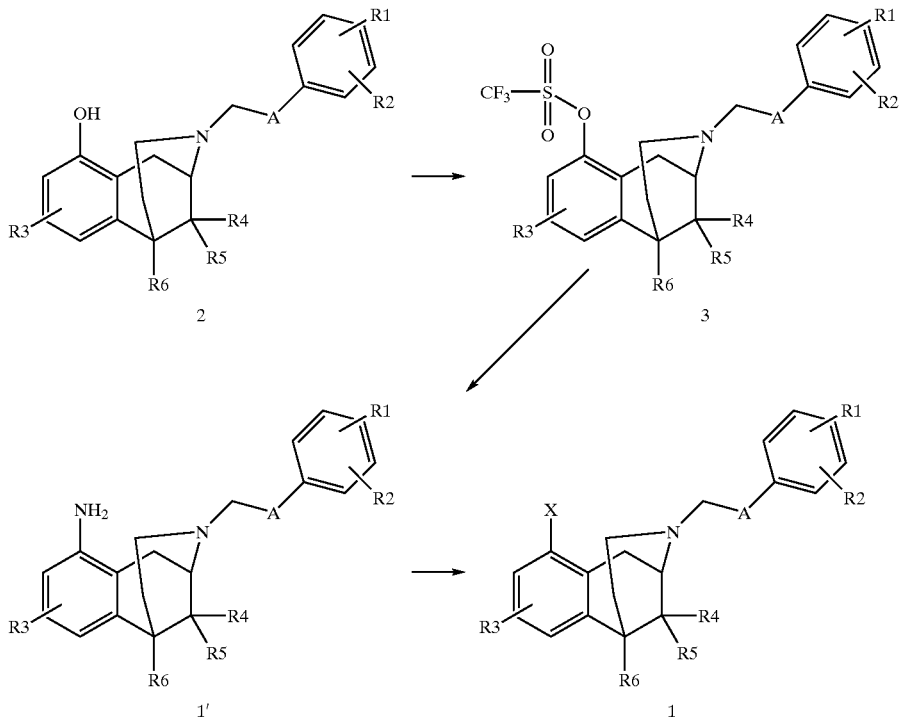

The key step is the conversion of the phenol 2 into the corresponding amino compound 1' (corresponding to compounds 1 wherein X is $NH_2$), which is done by means of a Buchwald reaction [J. P. Wolfe, J. Ahman, J. P. Sadighi, R. A. Singer, and S. L. Buchwald, THL 1997, 6367–6370].

The triflates 3 required for this reaction may be prepared from these compounds 2 with trifluoromethanesulfonic acid anhydride in the presence of an auxiliary base. Suitable auxiliary bases according to the invention include organic amines such as, for example, dimethylaminopyridine, pyridine, or tertiary amines such as trimethylamine, triethylamine, diisopropylethylamine, or DBU (diazabicycloundecene). Of the abovementioned amines, the tertiary amines are preferably used, and triethylamine is most preferably used as the auxiliary base. The reaction is carried out in aprotic, organic solvents, preferably in solvents selected from among dimethylformamide, dimethylacetamide, methylene chloride, toluene, or tetrahywhich may be used include, for example, ligands selected from among DPPF, BINAP, p-tolBINAP, $PPh_2$-CHMe-P $(tBu)_2$, phosphine-substituted ferrocenes, or triphenylphosphine. Tris(dibenzylideneacetone)dipalladium/BINAP is preferably used as the catalyst system. The reaction is preferably carried out with the exclusion of moisture and oxygen and preferably at elevated temperature. The solvent used is preferably refluxed during the reaction.

The imine adduct obtained as an intermediate can be converted by acid hydrolysis, preferably with dilute inorganic acids, most preferably with dilute hydrochloric acid, into the compounds according to the invention 1' (corresponding to compounds of formula 1 where X is $NH_2$). The products are purified by chromatography on silica gel or by crystallization, preferably by crystallization of the pharmacologically acceptable acid addition salts, e.g., the hydrochlorides.

As can be seen from the above remarks, the triflates of general formula 3 are of central importance in the synthesis of the compounds of general formula 1 according to the invention.

Accordingly, another aspect of the present invention relates to the intermediate compounds of general formula 3

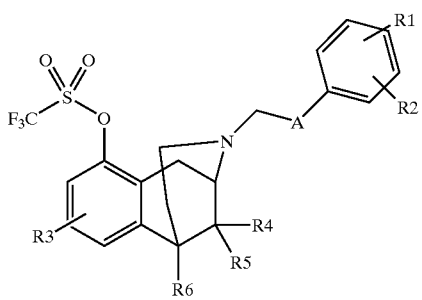

wherein the groups $R_1$, $R^2$, $R^3$, $R^4$, $R^5$, $R^6$, and A may be as hereinbefore defined.

In order to synthesize the compounds according to the invention of general formula 1 where X is not $NH_2$, the following process may be used.

Compounds of formula 1 wherein X is $NH-(C_1-C_6)$-alkyl or $N(C_1-C_6$-alkyl$)_2$ may be obtained by methods known per se by alkylation of 1', by reductive amination or by acylation, optionally in the presence of organic bases, with subsequent reduction.

For alkylation, the following method may be used. A compound of general formula 1' is dissolved in a polar organic solvent such as dimethylformamide, dimethylacetamide, methylene chloride, or tetrahydrofuran, preferably dimethylformamide or methylene chloride. The resulting solution is mixed with a base and a corresponding alkylating agent. Suitable bases include alkali and alkaline earth metal hydrides, preferably sodium hydride. Suitable alkylating agents include alkyl halides, such as alkyl chloride, alkyl bromide, particularly alkyl iodide and alkyl tosylates, mesylates, triflates, and dialkylsulfates. After conventional working up, the alkylated compounds of general formula 1 may be purified by chromatography on silica gel or by crystallization, optionally in the form of the pharmacologically acceptable addition salts thereof, preferably as hydrochlorides.

In order to prepare the compounds of general formula 1 by reductive amination, the amines 1' are mixed with aldehydes or ketones in the presence of acids such as dilute hydrochloric acid, dilute acetic acid, or dilute sulfuric acid, under otherwise conventional reaction conditions, with cooling, preferably at −50° C. to ambient temperature, most preferably between −30° C. and 0° C., and the Schiff bases or iminium salts thus formed as intermediates are then reduced. The reduction is carried out using metal hydrides such as sodium borohydride, $LiAlH_4$, Li-alkoxyhydrides, $NaBH_4$, $NaBHCN_3$, or $NaBH(OAc)_3$; sodium borohydride is preferably used. After working up in the usual way, the alkylated compounds of general formula I may be purified by chromatography on silica gel or by crystallization, optionally in the form of their pharmacologically acceptable acid addition salts thereof, preferably as hydrochlorides.

Compounds of formula 1 where X is $NHCO(C_1-C_6$-alkyl) may be prepared by methods known per se by acylating 1', preferably with acid chlorides or anhydrides. For this, the amino compound of formula 1' is suspended in an organic solvent, combined with an organic base and the desired acid chloride or anhydride is added. The mixture is kept at ambient temperature for 40 to 60 minutes, preferably 25 to 45 minutes at ambient temperature. Suitable organic solvents are dimethylformamide, dimethylacetamide, methylene chloride, toluene, or tetrahydrofuran; methylene chloride being preferred. Suitable organic bases are dimethylaminopyridine, pyridine, or tertiary amines, e.g., trimethylamine, triethylamine, diisopropylethylamine, and DBU (diazabicycloundecene). After working up, the products are purified by chromatography on silica gel or by crystallization, preferably by crystallization of the pharmacologically acceptable acid addition salts, e.g., the hydrochlorides.

Starting from the compounds of formula 1 with X is $NHCO(C_1-C_6$-alkyl) which may be obtained by the method described above, compounds of formula 1 with X is $NH(C_1-C_6$-alkyl), for example, may also be obtained by reduction with metal hydrides such as $LiAlH_4$, Li-alkoxyhydrides, $NaBH_4$, $NaBHCN_3$, or $NaBH(OAc)_3$, preferably sodium borohydride. These reactions are preferably carried out in ethereal organic solvents, preferably in tetrahydrofuran or dioxane in the presence of Lewis acids, preferably boron trifluoride etherate, at elevated temperature, preferably above 50° C., most preferably at the reflux temperature of the solvent used. After working up, the products are purified by chromatography on silica gel or by crystallization, preferably by crystallization of the pharmacologically acceptable acid addition salts, e.g., the hydrochlorides.

The formylated compounds of formula 1 (X=NHCOH) may be obtained, for example, by reacting the compounds of formula 1' with formic acid at elevated temperature, preferably at reflux temperature. After working up, the products are purified by chromatography on silica gel or by crystallization, preferably by crystallization of the pharmacologically acceptable acid addition salts, e.g., the hydrochlorides.

The fluorine-substituted compounds 1 (with X is F) may be obtained by methods known per se by diazotization of 1' and subsequent decoction with $BF_4-$. Preferably, the reaction is carried out with $NOBF_4$ as the diazotization and fluorination reagent in ethereal solvents, preferably in tetrahydrofuran or dioxane at elevated temperature, preferably above 50° C., most preferably at the reflux temperature of the solvent used. After working up, the products are purified by chromatography on silica gel or by crystallization, preferably by crystallization of the pharmacologically acceptable acid addition salts, e.g., the hydrochlorides.

The Examples which follow serve to illustrate the invention without restricting it to the compounds and methods disclosed by way of example.

EXAMPLE 1

(2R,6S,2S')-10-amino-3-[2(2,6-difluorophenylmethoxy) propyl]-1,2,3,4,5,6-hexahydro-6,11,11-trimethyl-2,6-methano-3-benzazocine Dihydrochloride 13.5 g (0.03 mol) of (2R,6S,2"S)-3-[2(2,6-difluorophenylmethoxy)propyl]-1,2,3,4,5,6-hexahydro-6,11,11-trimethyl-2,6-methano-3-benzazocin-10-ol are dissolved in 135 mL of dichloromethane, mixed with 30 mL of triethylamine and a spatula tip of 4-dimethylaminopyridine and cooled to −10° C. Then 6.8 mL of trifluoromethanesulfonic acid anhydride are added dropwise, the mixture is stirred for 1 hour at −10° C. and for a further 2 hours at room temperature (RT). The reaction mixture is poured onto ice, mixed with 50 mL of ammonia, the organic phase is separated off and washed once with 50 mL of water. The organic phase is dried, the solvent is eliminated in vacuo, the residue is taken up in 350 mL of toluene and mixed with 21.6 g of CsCO$_3$ and 10.8 g of benzophenonimine. Then nitrogen is passed through the suspension for 30 minutes, 1.2 g of BINAP and 0.6 g of tris(dibenzylideneacetone)dipalladium (0) are added and the mixture is refluxed for 6 h. After cooling, it is washed with 200 mL of water, the organic phase is dried and the solvent is eliminated in vacuo. The residue is taken up in ethanol and the hydrochloride is precipitated with ethereal HCl. Yield: 13.7 g (88%); melting point: 266° C.; [ ]$_D^{20}$=(−)37.0° (c=1 in MeOH).

The following compounds were obtained, inter alia, analogously to the procedure described above:

EXAMPLE 2

(2R,6S,2"S)-10-amino-3-[2-(benzyloxy)propyl]-1,2,3,4,5, 6-hexahydro-6,11,11-trimethyl-2,6-methano-3-benzazocine Dihydrochloride Melting point: 257° C.; [ ]$_D^{20}$=(−)29.3° (c=1 in MeOH).

EXAMPLE 3

(2R,6S, 11R,2"S)-10-amino-3-[2(2,6-difluorophenylmethoxy)propyl]-1,2,3,4,5,6-hexahydro-6, 11-dimethyl-2,6-methano-3-benzazocine Dihydrochloride Melting point: 232° C.; [ ]$_D^{20}$=(−)4.1° (c=1 in MeOH).

EXAMPLE 4

(2R,6S,11S,2"S)-10-amino-3-[2(2,6-difluorophenylmethoxy)propyl]-1,2,3,4,5,6-hexahydro-6, 11-dimethyl-2,6-methano-3-benzazocine Dihydrochloride Melting point: 267° C., [ ]$_D^{20}$=(−)2.4° (c=1 in MeOH).

EXAMPLE 5

(2R,6S)-10-amino-3-[2(2,6-difluorophenylmethoxy)ethyl]- 1,2,3,4,5,6-hexahydro-6,11,11-trimethyl-2,6-methano-3-benzazocine Dihydrochloride Melting point: 270° C.; [ ]$_D^{20}$=(−)77.4° (c=1 in MeOH).

EXAMPLE 6

(2R,6S,2"S,5"S)-10-amino-3-[5"-phenyltetrahydrofuran-2"-yl)methyl]-1,2,3,4,5,6-hexahydro-6,11,11-trimethyl-2,6-methano-3-benzazocine Dihydrochloride Melting point: 253° C.; [ ]$_D^{20}$=(−)135.40(c=1 in MeOH).

EXAMPLE 7

(2R,6S,2"S)-10-acetamino-3-[2(2,6-benzyloxy)propyl]-1,2, 3,4,5,6-hexahydro-6,11,11-trimethyl-2,6-methano-3-benzazocine Hydrochloride 2 mL of acetic anhydride are added to 1.1 g (2.4 mmol) of (2R,6S,2"S)-10-amino-3-[2-(benzyloxy)propyl]-1,2,3,4, 5,6-hexahydro-6,11,11-trimethyl-2,6-methano-3-benzazocine dihydrochloride and 5 mL of triethylamine in 50 mL of dichloromethane and the mixture is stirred for 0.5 hour at RT. It is then evaporated down in vacuo, 100 mL of ether are added and the mixture is washed twice with 50 mL of water. The organic phase is dried, the solvent is eliminated in vacuo, the residue is taken up in ether and the hydrochloride is precipitated with ethereal HCl. Yield: 0.8 g (73%); melting point: >100° C.; [ ]$_D^{20}$(−)56.5° (c=1 in MeOH).

The following compound was also obtained, inter alia, analogously to the method described above:

EXAMPLE 8

(2R,6S,2"S)-10-acetamino-3-[2(2,6-difluorophenylmethoxy)propyl]-1,2,3,4,5,6-hexahydro-6, 11,11-trimethyl-2,6-methano-3-benzazocine Hydrochloride Melting point: 125° C.; [ ]$_D^{20}$=(−)58.7° (c=1 in MeOH).

EXAMPLE 9

(2R,6S,2"S)-10-formylamino-3-[2(2,6-difluorophenylmethoxy)propyl]-1,2,3,4,5,6-hexahydro-6, 11,11-trimethyl-2,6-methano-3-benzazocine Hydrochloride 0.5 g (1.2 mmol) of (2R,6S,2"S)-10-amino-3-[2(2,6-difluorophenylmethoxy)propyl]-1,2,3,4,5,6-hexahydro-6, 11,11-trimethyl-2,6-methano-3-benzazocine are combined with 10 mL of 97% formic acid and refluxed for 1 hour. The mixture is then concentrated by evaporation in vacuo, the residue is combined with ice and 50 mL of ammonia and extracted twice with 50 mL of ethyl acetate. The combined organic phase is washed with 30 mL of water, dried and the solvent is eliminated in vacuo. The residue is taken up in ether and the hydrochloride is precipitated with ethereal HCl. Yield: 0.3 g (52%); melting point: amorphous; [ ]$_D^{20}$=(−)41.60(c=1 in MeOH).

EXAMPLE 10

(2R,6S,2"S)-10-methylamino-3-[2(2,6-difluorophenylmethoxy)propyl]-1,2,3,4,5,6-hexahydro-6, 11,11-trimethyl-2,6-methano-3-benzazocine Dihydrochloride 1.0 g (2.4 mmol) of (2R,6S,2"S)-10-amino-3-[2(2,6-difluorophenylmethoxy)propyl]-1,2,3,4,5,6-hexahydro-6, 11,11-trimethyl-2,6-methano-3-benzazocine are dissolved in 10 mL of ethyl acetate and combined with 1 mL of triethylamine and 1 mL of trifluoroacetic acid anhydride. After 10 minutes, the mixture is washed twice with 10 mL of water, the organic phase is dried and the solvent is eliminated in vacuo. The residue is taken up in 10 mL of dimethylacetamide and mixed with 0.5 g of NaH. After 15 minutes, 1 mL of methyl iodide is added and the mixture is stirred for 1 hour at 50° C. The solvent is then eliminated in vacuo, the residue is combined with 20 mL of methanol and 2 mL of 20% NaOH and stirred for 30 minutes at 60° C. The solution is again concentrated by evaporation in vacuo, the residue is mixed with 50 mL of water and extracted twice with 100 mL of ether. The combined organic phase is dried, the solvent is eliminated in vacuo and the residue is chromatographed on silica gel. The appropriate fractions are combined and the hydrochloride is precipitated with ethereal HCl. Yield: 0.4 g (35%); melting point: 243° C.; [ ]$_D^{20}$=(−) 20.5° (c=1 in MeOH).

EXAMPLE 11

(2R,6S,2"S)-10-dimethylamino-3-[2-(2,6-difluorophenylmethoxy)propyl]-1,2,3,4,5,6-hexahydro-6, 11,11-trimethyl-2,6-methano-3-benzazocine Dihydrochloride A suspension of 0.4 g (1 mmol) of (2R,6S,2"S)-10-amino-3-[2-(2,6-difluorophenylmethoxy)propyl]-1,2,3,4,5,6-hexahydro-6,11,11-trimethyl-2,6-methano-3-benzazocine and 0.3 g of NaBH$_4$ in 7 mL of THF is added batchwise to a solution of 0.6 mL of 37% formalin and 1.2 mL of 3N H$_2$SO$_4$, cooled to −10° C. After it has all been added the mixture is reacted for a further 10 minutes, ammonia is added and the resulting mixture is extracted twice with 20 mL of ethyl acetate. The organic phase is dried, the solvent is eliminated in vacuo, the residue taken up in ether and the hydrochloride is precipitated with ethereal HCl. Yield: 0.5 g (97%); melting point: 125° C.; [ ]$_D^{20}$=(−)20.0° (c=1 in MeOH).

EXAMPLE 12

(2R,6S,2"S)-10-ethylamino-3-[2(2,6-difluorophenylmethoxy)propyl]-1,2,3,4,5,6-hexahydro-6, 11,11-trimethyl-2,6-methano-3-benzazocine Dihydrochloride 1.1 g (2.4 mmol) of (2R,6S,2"S)-10-acetamino-3-[2(2,6-difluorophenylmethoxy)propyl]-1,2,3,4,5,6-hexahydro-6, 11,11-trimethyl-2,6-methano-3-benzazocine are dissolved in 30 mL of THF, combined with 0.5 g of NaBH$_4$ and 1.5 mL of BF$_3$-etherate and refluxed for 6 hours. The mixture is left to cool, 30 mL of MeOH and 60 mL of 2 N HCl are added and the resulting mixture is refluxed for a further 30 minutes. Then the solvent is eliminated in vacuo, the residue is combined with concentrated ammonia and extracted twice with 30 mL of ethyl acetate. The combined organic phase is washed once with 20 mL of water, dried and the solvent is eliminated in vacuo. The residue is taken up in acetone and the hydrochloride is precipitated with ethereal HCl. Yield: 0.95 g (89%); melting point: 242° C.; $[\ ]_D^{20}=(-)24.8°$ (c=1 in MeOH).

EXAMPLE 13

(2R,6S,2"S)-10-Fluoro-3-[2(2,6-difluorophenylmethoxy) propyl]-1,2,3,4,5,6-hexahydro-6,11,11-trimethyl-2,6-methano-3-benzazocine Hydrochloride 1.5 g (3.6 mmol) of (2R,6S,2"S)-10-amino-3-[2(2,6-difluorophenylmethoxy)propyl]-1,2,3,4,5,6-hexahydro-6,11,11-trimethyl-2,6-methano-3-benzazocine are placed in 30 mL of dioxane, combined with 3 g of $NOBF_4$ in 30 mL of dioxane and stirred for 1 hour at 90° C. The solvent is then eliminated in vacuo, the residue is combined with 50 mL of ethyl acetate and washed once with 30 mL of dilute ammonia and 30 mL of water. The combined organic phase is dried, the solvent is eliminated in vacuo and the residue is chromatographed on silica gel. The appropriate fractions are combined and the hydrochloride is precipitated with ethereal HCl. Yield: 0.5 g (33%); melting point: 190° C.; $[\ ]_D^{20}(-)27.3°$ (c=1 in MeOH).

The compounds according to the invention may be administered orally, transdermally, by inhalation, or parenterally. The compounds according to the invention occur as active ingredients in conventional preparations, for example, in compositions which consist essentially of an inert pharmaceutical carrier and an effective dose of the active substance, such as for example tablets, coated tablets, capsules, lozenges, powders, solutions, suspensions, emulsions, syrups, suppositories, transdermal systems, etc. An effective dose of the compounds according to the invention is between 1 and 1000 mg/dose, preferably between 1 and 500 mg/dose, most preferably between 5 and 300 mg/dose for oral administration, and between 0.001 and 50 mg/dose, preferably between 0.1 and 10 mg/dose for intravenous, subcutaneous, or intramuscular administration. For inhalation, according to the invention, solutions containing 0.01% to 1.0% active substance, preferably 0.1% to 0.5% active substance are suitable. For administration by inhalation, the use of powders is preferred. It is also possible to use the compounds according to the invention as a solution for infusion, preferably in a physiological saline or nutrient saline solution.

The compounds according to the invention may be used on their own or in conjunction with other active substances according to the invention, optionally also in conjunction with other pharmacologically active substances. Suitable preparations include for example tablets, capsules, suppositories, solutions, elixirs, emulsions, or dispersible powders.

Suitable tablets may be obtained, for example, by mixing the active substance(s) with known excipients, for example, inert diluents such as calcium carbonate, calcium phosphate, or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number or layers to achieve delayed release, possibly using the excipients mentioned above for the tablets.

Syrups or elixirs containing the active substances or combinations thereof according to the invention may additionally contain a sweetener such as saccharine, cyclamate, glycerol, or sugar and a flavor enhancer, e.g., a flavoring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection are prepared in the usual way, e.g., with the addition of preservatives such as p-hydroxybenzoates, or stabilizers such as alkali metal salts of ethylenediamine tetraacetic acid, and transferred into injection vials or ampoules.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

A therapeutically effective daily dose is between 1 mg and 800 mg, preferably between 10 mg and 300 mg per adult.

The Examples which follow illustrate the present invention without restricting its scope:

Examples of Pharmaceutical Formulations

| A. Tablets | |
| --- | --- |
| Component | Amount per tablet |
| active substance | 100 mg |
| lactose | 140 mg |
| corn starch | 240 mg |
| polyvinylpyrrolidone | 15 mg |
| magnesium stearate | 5 mg |
| TOTAL | 500 mg |

The finely ground active substance, lactose, and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B. Tablets | |
| --- | --- |
| Component | Amount per tablet |
| active substance | 80 mg |
| lactose | 55 mg |
| corn starch | 190 mg |
| microcrystalline cellulose | 35 mg |
| polyvinylpyrrolidone | 15 mg |
| sodium-carboxymethyl starch | 23 mg |
| magnesium stearate | 2 mg |
| TOTAL | 400 mg |

The finely ground active substance, some of the corn starch, lactose, microcrystalline cellulose, and polyvinylpyrrolidone are mixed together, the mixture is screened and worked with the remaining corn starch and water to form a granulate which is dried and screened. The sodium-carboxymethyl starch and the magnesium stearate are added and mixed in and the mixture is compressed to form tablets of a suitable size.

| C. Coated Tablets | |
|---|---|
| Component | Amount per coated tablet |
| active substance | 5 mg |
| lactose | 30 mg |
| corn starch | 41.5 mg |
| polyvinylpyrrolidone | 3 mg |
| magnesium stearate | 0.5 mg |
| TOTAL | 80 mg |

The active substance, corn starch, lactose, and polyvinylpyrrolidone are thoroughly mixed and moistened with water. The moist mass is pushed through a screen with a 1 mm mesh size, dried at about 45° C. and the granules are then passed through the same screen. After the magnesium stearate has been mixed in, convex tablet cores with a diameter of 6 mm are compressed in a tablet-making machine. The tablet cores thus produced are coated in known manner with a covering consisting essentially of sugar and talc. The finished coated tablets are polished with wax.

| D. Capsules | |
|---|---|
| Component | Amount per capsule |
| active substance | 50 mg |
| corn starch | 268.5 mg |
| magnesium stearate | 1.5 mg |
| TOTAL | 320 mg |

The substance and corn starch are mixed and moistened with water. The moist mass is screened and dried. The dry granules are screened and mixed with magnesium stearate. The finished mixture is packed into size 1 hard gelatine capsules.

| E. Ampoule Solution | |
|---|---|
| Component | Amount per ampoule |
| active substance | 50 mg |
| sodium chloride | 50 mg |
| water for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilized and sealed by fusion. The ampoules contain 5 mg, 25 mg, and 50 mg of active substance.

| F. Suppositories | |
|---|---|
| Component | Amount per suppository |
| active substance | 50 mg |
| Solid fat | 1650 mg |
| TOTAL | 1700 mg |

The hard fat is melted. At 40° C., the ground active substance is homogeneously dispersed. It is cooled to 38° C. and poured into slightly chilled suppository molds.

We claim:

1. A compound of general formula 1

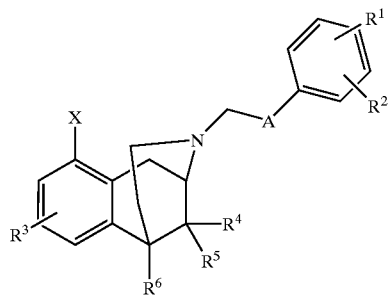

wherein:

$R^1$ and $R^2$, which are identical or different, are each hydrogen or F;

$R^3$ is hydrogen or methyl;

$R^4$ is hydrogen $R^5$ and $R^6$ are each methyl;

X is $NH_2$, NH-(methyl), N(methyl)$_2$, NH—COH, or NH—COMe; and

A is —CH(Methyl)-O—CH$_2$—, —(CH$_2$)$_2$—O—CH$_2$—, or

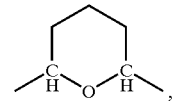

the racemates thereof, the enantiomers thereof, the diastereomers thereof, and mixtures thereof, and the pharmacologically acceptable acid addition salts thereof.

2. The compound of general formula 1 according to claim 1, wherein:

$R^3$ is methyl, the racemates thereof, the enantiomers thereof, the diastereomers thereof, and mixtures thereof, and the pharmacologically acceptable acid addition salts thereof.

3. The compound of general formula 1 according to claim 1, wherein:

$R^3$ is hydrogen; and

A is —CH(methyl)-O—CH$_2$—, the racemates thereof, the enantiomers thereof, the diastereomers thereof, and mixtures thereof, and the pharmacologically acceptable acid addition salts thereof.

4. A compound of general formula 1

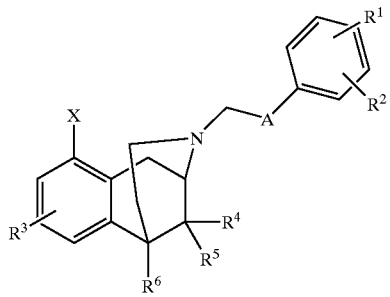

wherein:
R$^1$ and R$_1$, which are identical or different, are each hydrogen or F;
R$^3$ is hydrogen or methyl;
R$^5$ is hydrogen;
R$^4$ and R$^6$ are each methyl;
is NH$_2$, NH-(methyl), N(methyl)$_2$, NH—COH, or NH—COMe; and
A is —CH(Methyl)-O—CH$_2$—, —(CH$_2$)$_2$—O—CH$_2$—, or

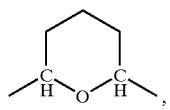

the racemates thereof, the enantiomers thereof, the diastereomers thereof, and mixtures thereof, and the pharmacologically acceptable acid addition salts thereof.

5. The compound of general formula 1 according to claim 4, wherein:
R$^3$ is methyl;
the racemates thereof, the enantiomers thereof, the diastereomers thereof, and mixtures thereof, and the pharmacologically acceptable acid addition salts thereof.

6. The compound of general formula 1 according to claim 4, wherein:
R$^3$ is hydrogen,
the racemates thereof, the enantiomers thereof, the diastereomers thereof, and mixtures thereof, and the pharmacologically acceptable acid addition salts thereof.

7. The compound of general formula 1 according to claim 6, wherein:
A is —CH(methyl)-O—CH$_2$—,
the racemates thereof, the enantiomers thereof, the diastereomers thereof, and mixtures thereof, and the pharmacologically acceptable acid addition salts thereof.

8. A pharmaceutical preparation comprising:
(a) a compound of formula 1 according to one of claims 1–7; and
(b) one or more conventional excipients or carriers.

9. A method of blocking the voltage-dependent sodium channel in a host by administering a compound of formula 1 according to one of claims 1–7 to a host.

10. A method of treating arrhythmias, spasms, cardiac and cerebral ischaemia, pain, and neurodegenerative diseases, the method comprising administering to a host a therapeutically acceptable amount of a compound of formula 1 according to one of claims 1–7.

11. A method of treating epilepsy, hypoglycaemia, hypoxia, anoxia, brain trauma, brain oedema, cerebral stroke, perinatal asphyxia, degeneration of the cerebellum, amyotrophic lateral sclerosis, Huntington's disease, Alzheimer's disease, Parkinson's disease, cyclophrenia, hypotonia, cardiac infarct, cardiac rhythm disorders, angina pectoris, chronic pain, neuropathic pain, or local anesthesia, the method comprising administering to a host a therapeutically acceptable amount of a compound of formula 1 according to one of claims 1–7.

12. A method for preparing a compound of general formula 1

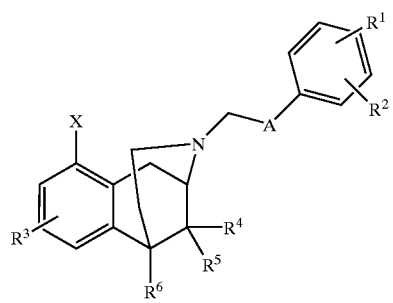

wherein:
R$^1$ and R$^2$, which may be identical or different, are each hydrogen, C$_1$–C$_6$-alkyl, C$_1$–C$_6$-alkyloxy, OH, F, Cl, or Br;
R$^3$ is hydrogen, F, Cl, Br, methyl, ethyl, OH, or methoxy;
R$^4$, R$^5$, and R$^6$, which may be identical or different, are each hydrogen, methyl, or ethyl;
is NH$_2$;
A is —(CH$_2$)$_3$—, —CH$_2$—CH$_2$—O—, —CH$_2$—O—CH$_2$—, —(CH$_2$)$_4$—, —CH(C$_1$–C$_6$-alkyl)-O—CH$_2$—, —(CH$_2$)$_2$—O—CH$_2$13 , —(CH$_2$)$_3$—O—, —(CH$_2$)$_5$—, —CH$_2$—O—(CH$_2$)$_3$13 , 13 (CH$_2$)$_2$—O—(CH$_2$)$_2$—, —(CH$_2$)$_3$—O—CH$_2$—, —(CH$_2$)$_4$—O—, —CH$_2$—O—CH$_2$—CH$_2$—O—,

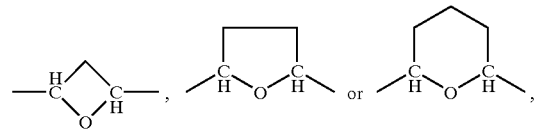

the racemates thereof, the enantiomers thereof, the diastereomers thereof, and mixtures thereof, and the pharmacologically acceptable acid addition salts thereof, the method comprising reacting a compound of general formula 3

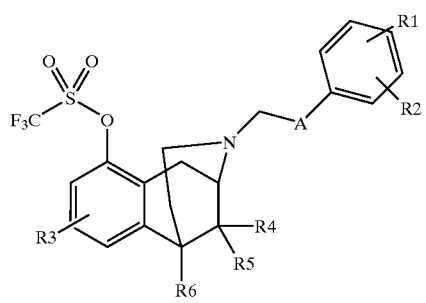

wherein the groups R$^1$, R$^2$, R$^3$, R$^4$, R$_5$, R$^6$, and A have the meanings given above, with a source of nitrogen in an aromatic solvent with palladium catalysis.

13. A compound of general formula 3

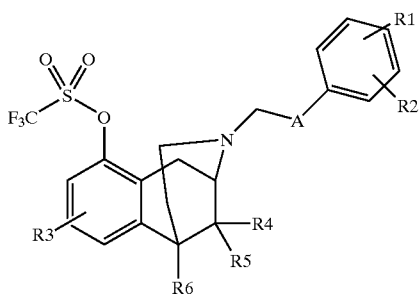

wherein:
R$^1$ and R$^2$, which may be identical or different, are each hydrogen, C$_1$–C$_6$-alkyl, C$_1$–C$_6$-alkyloxy, OH, F, Cl, or Br;
R$^3$ is hydrogen, F, Cl, Br, methyl, ethyl, OH, or methoxy;
R$^4$, R$^5$, and R$^6$, which may be identical or different, are each hydrogen, methyl, or ethyl;
X is NH$_2$, NH-(C$_1$–C$_6$-alkyl), N(C$_1$–C$_6$-alkyl)$_2$, the two C$_1$–C$_6$-alkyl groups of which may be identical or different, NH—COH, NH—CO(C$_1$–C$_6$-alkyl), or F;
A is —(CH$_2$)$_3$—, —CH$_2$—CH$_2$—O—, —CH$_2$—O—CH$_2$—, —(CH$_2$)$_4$—, —CH(C$_1$–C$_6$-alkyl)-O—CH$_2$—, —(CH$_2$)$_2$—O—CH$_2$13 , —(CH$_2$)$_3$—O—, —(CH$_2$)$_5$—, —CH$_2$—O—(CH$_2$)$_3$—, —(CH$_2$)$_2$—O—(CH$_2$)$_2$—, —(CH$_2$)$_3$—O—CH$_2$—, —(CH$_2$)$_4$—O—, —CH$_2$—O—CH$_2$—CH$_2$—O—,

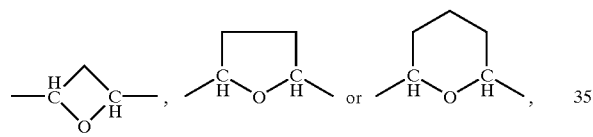

the racemates thereof, the enantiomers thereof, the diastereomers thereof, and mixtures thereof, and the pharmacologically acceptable acid addition salts thereof.

14. A method for preparing a compound of general formula 1

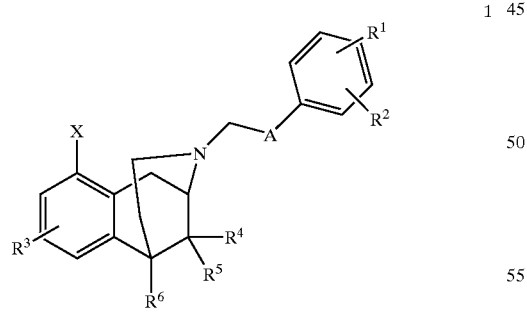

wherein:
R$^1$ and R$^2$, which may be identical or different, are each hydrogen, C$_1$–C$_6$-alkyl, C$_1$–C$_6$-alkyloxy, OH, F, Cl, or Br;

R$^3$ is hydrogen, F, Cl, Br, methyl, ethyl, OH, or methoxy;
R$^4$, R$^5$, and R$^6$, which may be identical or different, are each hydrogen, methyl, or ethyl;
X is NH-(C$_1$–C$_6$-alkyl), N(C$_1$–C$_6$-alkyl)$_2$, the two C$_1$–C$_6$-alkyl groups of which may be identical or different, NH—COH, NH—CO(C$_1$–C$_6$-alkyl), or F;
A is —(CH$_2$)$_3$—, —CH$_2$—CH$_2$—O—, —CH$_2$—O—CH$_2$—, —(CH$_2$)$_4$—, —CH(C$_1$–C$_6$-alkyl)-O—CH$_2$—, —(CH$_2$)$_2$—O—CH$_2$13 , —(CH$_2$)$_3$—O—, —(CH$_2$)$_5$—, —CH$_2$—O—(CH$_2$)$_3$—, —(CH$_2$)$_2$—O—(CH$_2$)$_2$—, —(CH$_2$)$_3$—O—CH$_2$—, —(CH$_2$)$_4$—O—, —CH$_2$—O—CH$_2$—CH$_2$—O—,

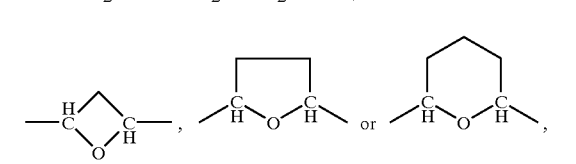

the racemates thereof, the enantiomers thereof, the diastereomers thereof, and mixtures thereof, and the pharmacologically acceptable acid addition salts thereof, the method comprising:
reacting a compound of formula 1, wherein the groups R$_1$, R$^2$, R$^3$, R$^4$, R$^5$, R$^6$, and A have the meanings given above and X is NH$_2$:
(a) with a base and an alkylating agent, in a polar organic solvent, to obtain the compound of general formula 1, wherein X is NH-(C$_1$–C$_6$-alkyl) or N(C$_1$–C$_6$-alkyl)$_2$; or
(b) with aldehydes or ketones, with cooling, in the presence of acids, to obtain a Schiff base or an iminium salt and subsequently reducing the Schiff base or the iminium salt obtained with metal hydrides to obtain the compound of general formula 1, wherein X is NH-(C$_1$–C$_6$-alkyl) or N(C$_1$–C$_6$-alkyl)$_2$; or
(c) with an acid chloride or anhydride, in the presence of a base, to obtain the compound of general formula 1, wherein X is NHCO(C$_1$–C$_6$-alkyl); or
(d) with an acid chloride or anhydride, in the presence of a base, to obtain the compound of general formula 1, wherein X is NHCO(C$_1$–C$_6$-alkyl), and subsequently reducing the compound of general formula 1, wherein X is NHCO(C$_1$–C$_6$-alkyl), with a metal hydride, using a Lewis acids as a catalyst, to obtain the compound of general formula 1, wherein X is NH-(C$_1$–C$_6$-alkyl) or N(C$_1$–C$_6$-alkyl)$_2$; or
(e) with formic acid at elevated temperature to obtain the compound of general formula 1, wherein X is NHCOH; or
(f) by diazotization and subsequent decoction with BF$_4^-$ to obtain the compound of formula 1, wherein X is F.

* * * * *